(12) United States Patent
Huang et al.

(10) Patent No.: US 9,052,306 B2
(45) Date of Patent: Jun. 9, 2015

(54) CODING MODULE, BIO MEASURING METER AND SYSTEM FOR OPERATING BIO MEASURING METER

(75) Inventors: Chun-Mu Huang, Taichung County (TW); Mao-Sung Huang, Taichung County (TW); Cheng-Chieh Chuang, Taichung County (TW)

(73) Assignee: BIONIME CORPORATION, Taichung County (TW)

( * ) Notice: Subject to any disclaimer, the term of this patent is extended or adjusted under 35 U.S.C. 154(b) by 857 days.

(21) Appl. No.: 11/690,407

(22) Filed: Mar. 23, 2007

(65) Prior Publication Data

US 2008/0229850 A1 Sep. 25, 2008

(51) Int. Cl.
*G01N 33/50* (2006.01)
*G01N 33/487* (2006.01)

(52) U.S. Cl.
CPC ................................ *G01N 33/48771* (2013.01)

(58) Field of Classification Search
CPC .............................................. G01N 33/48771
See application file for complete search history.

(56) References Cited

U.S. PATENT DOCUMENTS

| | | | | |
|---|---|---|---|---|
| 3,733,862 | A * | 5/1973 | Killmeyer | 70/277 |
| 4,371,759 | A | 2/1983 | Clark, Jr. | |
| 4,721,956 | A * | 1/1988 | Demster | 340/5.67 |
| 4,954,087 | A * | 9/1990 | Lauks et al. | 439/71 |
| 5,035,704 | A | 7/1991 | Lambert et al. | |
| 5,053,199 | A | 10/1991 | Keiser et al. | |
| 5,096,669 | A * | 3/1992 | Lauks et al. | 204/403.02 |
| 5,366,609 | A | 11/1994 | White et al. | |
| 6,773,671 | B1 | 8/2004 | Lewis et al. | |
| 8,262,995 | B2 | 9/2012 | Manser et al. | |
| 2006/0290488 | A1 | 12/2006 | Huang | |
| 2007/0235330 | A1 | 10/2007 | Lyuu | |

FOREIGN PATENT DOCUMENTS

| | | |
|---|---|---|
| DE | 3149461 | 8/1982 |
| DE | 102007027191 | 12/2008 |
| EP | 0764469 | 3/1997 |
| EP | 1729128 | 6/2006 |
| TW | I265677 | 11/2006 |
| TW | 200739065 | 10/2007 |

* cited by examiner

*Primary Examiner* — Paul Hyun
(74) *Attorney, Agent, or Firm* — Volpe and Koenig, P.C.

(57) ABSTRACT

A bio-measuring meter is provided. The bio-measuring meter includes a receptacle receiving a sample strip for the bio-measuring meter; and a figured piece identifying device comprising plural switches for receiving a figured piece, wherein at least one of the plural switches is switched by the figured piece to generate a current signal, and a datum of the sample strip is adjusted by a predefined respective parameter for the current signal.

10 Claims, 15 Drawing Sheets

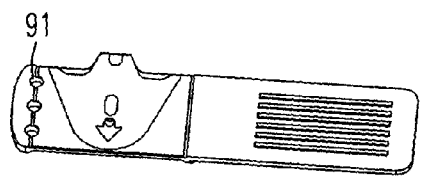
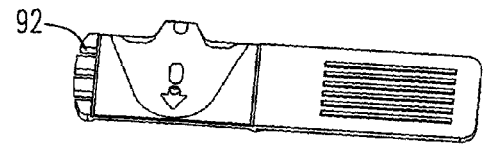
Fig. 9a          Fig. 9b
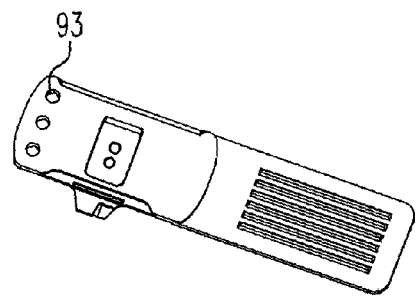
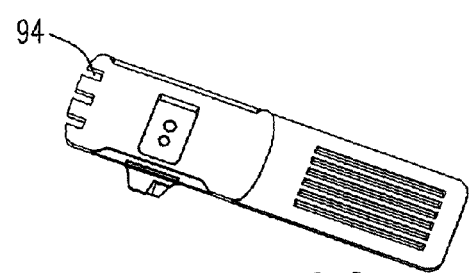
Fig. 9c          Fig. 9d
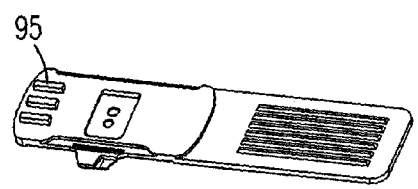
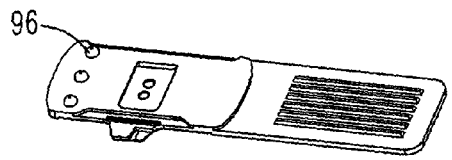
Fig. 9e          Fig. 9f
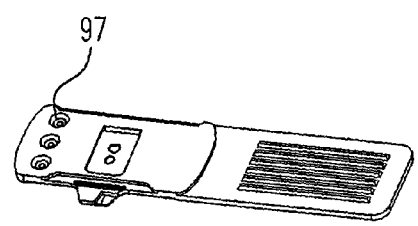
Fig. 9g

CODING MODULE, BIO MEASURING METER AND SYSTEM FOR OPERATING BIO MEASURING METER

FIELD OF THE INVENTION

The present invention relates to bio measuring meters for determining the presence of an analyte in a biological sample, and more particularly, to a bio measuring meter whose operation is controlled by a code provided by a removably pluggable coding module. The present invention further relates to a coding module pluggable into a bio measuring meter for receiving a sample strip. The coding module defines at least one code, the code ciphering at least one property that is employed in controlling the operation of the meter, for example by controlling the operation of the meter. The invention further relates to a set of coding modules, to a method for producing coding modules, to a bio measuring system, to a bio measuring test set and to a method for operating a bio measuring meter in accordance with the claims.

BACKGROUND OF THE INVENTION

Bio measuring meters applied for detecting substances contained in blood to be analyzed, such as glucose or cholesterol, use a disposable sample strip. The sample strip has a reaction zone allowing blood to be placed thereon. The operation is controlled by a microprocessor. By execution of various methods, analysis results of the measurement are obtained.

For processing the sample measurement and the analysing routines the bio measuring meter needs certain parameter values which determine thresholds, time intervals, control numbers and calibration curve attributes.

Usually it is necessary to calibrate measuring devices in order to compensate for variations from lot to lot of the manufactured sample strip. Various techniques have been suggested for encoding information into the sample strip, as disclosed by U.S. Pat. No. 5,053,199 and references cited therein. This may e.g. be electronically encoded information on a carrier having an optical bar code, a magnetizable film, a perforated strip, a fluorogens or an electrically conductive medium on a foil.

Each of such known sample strips has to be furnished with an in-formation code, which is an additional manufacturing step and thus an expensive effort for a disposable device.

Other conventional measuring meters use an additional coding module or code key designed and inserted into a receptacle similar to the slot for the sample strip.

When performing a measurement, the memory key has to be inserted in the measuring meter before using a new batch of sample strips. Preferably the coding module remains inserted during the measurement or even all the time for the same batch of sample strips.

Based on the data or the code provided by the coding module the operation method, parameters or algorithms are chosen and a correct measurement result is obtained.

U.S. Pat. No. 5,366,609 and documents cited therein disclose bio measuring meters which have pluggable ROM coding modules that enable re-configuration of test methods and parameters employed by the meter. Threshold potentials, test times, delay periods and other pertinent test methods and constants may be entered and/or altered.

The main purpose of the coding module still is to provide information about the type of sample strip. For each new batch of sensor strips, new related information is needed.

As sample strips are disposable, preferably coding modules are disposable too. Costs for the module are therefore an important factor.

In a co-pending application, a coding module and bio measuring meter are presented, wherein the code is represented by a parameter value of an electrical component having a determined characteristic, such as a resistor or a capacitor. In comparison with the use of integrated circuits, the use of electrical components reduces the complexity and cost of the design. Thus, some of the drawbacks of the state of the art are overcome. However, the costs due to components and fabrication are still relatively high. Furthermore, electrical components present a risk of being influenced by a contamination of biological samples. Cleaning of such a code key is not easily feasible.

It is therefore an object of the invention to overcome the drawbacks of the prior art, especially to avoid the usage of memory IC chip technology for storing codes on coding modules, and to provide a coding module, a set of coding modules, a method for producing a coding module, a bio measuring meter with pluggable coding module, a bio measuring system, a bio measuring test set and a method for operating a bio measuring meter, which are not sensible with regard to a pollution caused by a biological sample and which can be produced cost-effectively.

SUMMARY OF THE INVENTION

In accordance with the present invention, a coding module is presented, which is connectable with a bio measuring meter for receiving a sample strip. The coding module defines at least one code. The code ciphers at least one property that is usable during operation of the meter. The at least one code is represented by at least one figured element.

According to the present invention, a figured element is an element having an outer structure which is mechanically ascertain-able. The at least one figured element typically can have an identifiable form, shape or surface texture. Preferably, the at least one figured element is arranged at a predefined position of the coding module. These positions define a coding area on the coding module.

The property usable on operation of the meter can be a set of parameter values that is employed in controlling the operation of the meter, for example by defining an evaluation curve or a parameter value for the choice of a predefined evaluation procedure or an input for a microprocessor routine.

A coding module being connectable with a bio measuring meter can be brought into measuring contact with the meter once, repeatedly or can remain attached thereto.

One advantage of using figured elements for encoding information is that the coding module can be integrally formed. No further steps for adding or fixing electric or electronic components are necessary which results in a cost-effective fabrication.

Whereas in the conventional coding modules, the code is mostly represented by electromagnetic characteristics, and the figured elements according to the present invention have mechanical characteristics which are not influenced by electromagnetic fields or chemical pollution.

The coding module according to the present invention can be completely free of electronic or electromagnetic components for coding purposes, which leads to a cost reduction by a saving of components and additional fabrication steps. Because of the lack of such components, the module can easily be cleaned. However, electronic or electric contacts may be present for other purposes.

Preferably, the at least one figured element is able to activate a switch and/or to engage with a switch on a meter. The switch can be activated directly, for example by the figured element closing or interrupting an electrical connection. Alternatively the switch could be activated indirectly, for example electro-magnetically based on e.g. optical, tactile or electric detection of the figured element.

The coding area of the coding module could also be coated with a second material, for example a conductive layer, thus resulting in an electro-magnetically or optically detectable pattern.

To allow the engagement with a switch on the bio measuring meter the at least one figured element is preferably formed by a projecting element, for example a protrusion, a tine, a tooth and/or pin, and/or an incising element, for example a cut, a recess and/or a hole. Figured elements of these types can simply be added to a basic form of a coding module but can also easily be formed in a production step when a coding module is integrally made in one piece. Moreover, the coding module can be integrally formed with the sample strip.

In a preferred embodiment, the at least one code is represented by a number and an arrangement of figured elements, preferably representing a binary code of 1 to 10 digits, more preferably of five digits. Thus the presence or the absence of a certain shaped element can simply be translated to a zero or one in a binary code and thus to one or more numbers. These numbers can for example be used for accessing data from a look up table such as to receive associated parameter values.

The coding module can have a receptacle able to receive the sample strip. The receptacle can allow a direct electrical coupling between the sample strip and the bio measuring meter. Alternatively the coding module can have an electrical coupling for connecting the sample strip and the bio measuring meter.

In both alternatives, the samples strip might come into contact with the coding module which leads to the danger of a pollution caused by the biologic sample. The coding represented by at least one figured element is not disturbed by a possible contamination with biologic sample or analyte. In case of a contamination, the function of the coding module is not affected. Furthermore, a one piece coding module can easily be cleaned and sanitized without influencing the coding elements and thus a continued use is allowed.

According to a further aspect of the invention, there is provided a set of coding modules, particularly of the above described type, with at least two types of coding modules, wherein the coding modules differ in the number, in the shape and/or in the arrangement of their figured elements. Thus, each coding module defines a different code, ciphering parameter values being related to a certain sample strip batch.

After fabrication of a series of samples strips, the samples strips can be measured and be divided into batches, which batches are associated with certain members of the set of coding modules.

According to a further aspect of the invention, there is provided a method for producing a coding module or a set of coding modules, preferably of the above described type comprising the step of moulding of a coding module in a mould, wherein the mould is designed to provide at least one figured element.

The coding module can e.g. be injection moulded. Other processes, e.g. compression moulding, are also possible. The figured elements can be integrally formed or elements can be formed which can be subsequently used to form figured elements, for example a perforation which allows to remove parts of the coding area.

To fabricate a set of coding modules, the mould can be completely exchanged and the mould can be replaced by a different one featuring different figured elements. Preferably, the mould is modified only on parts.

For example, only the part of the mould forming the at least one figured element representing the code is replaced by a different part designed to form a further code. After moulding coding modules with a second code, the mould can be modified again. By using this method, it is possible to fabricate a set of coding modules.

Since for different encodings only parts of the mould have to be exchanged, this method is cost-effective with regard to the investment and preproduction cost.

Instead of exchanging or modifying the mould to fabricate coding modules with different encodings, it is also possible to fabricate a basic coding module preformed by moulding.

In a second fabrication step, a code representation is provided by adding, removing and/or changing at least one figured element, wherein the code representation corresponds to a certain type of sample strips.

This adaptation can be carried out by a mechanical post processing, for example by drilling, cutting or removing at least one prepared part of the coding area.

According to another aspect of the invention, a bio measuring meter for receiving a sample strip is provided, the bio measuring meter having a receptacle able to accept a pluggable coding module. The bio measuring meter comprises means for receiving information from the coding module defining at least one code. The means comprises means for measuring at least one figured element representing the code.

The coding module is preferably of the above described type, wherein the code is represented by a number an arrangement of figured elements.

The bio measuring meter is provided with information about the sample strip batch by the code on the coding module.

The code can be a simple binary code, defining a code number and being interpreted as one of a variety of sets of parameter values stored in the bio measuring meter. The encoding can be made more complex by using a bigger number of figured elements or by different types of figured elements, such as holes and protrusions.

The determination of the code based on measuring of the figured elements and the translation of the code into parameter values used during operation is performed by the bio measuring meter. The coding module is only a carrier of the code. The bio measuring meter has the capability of reading the code, decoding and using the information. The parameter values can be derived from the code by a microprocessor routine or can be extracted using a look-up table stored in a memory of the bio measuring meter.

Preferably the bio measuring meter comprises mechanical, electromagnetic and/or optical means for reading the code, measuring the at least one figured element of the coding module.

In a preferred embodiment, the bio measuring meter comprises at least one switch, activable by the at least one figured element. More preferably, the bio measuring meter comprising as many switches as positions for figured elements are arranged on the coding module, such that each position of a figured element corresponds to a switch and each figured element interacts with a corresponding switch.

The bio measuring meter may have different receptacles for the sample strips and the coding module. Alternatively the bio measuring meter may comprise one receptacle able to accept a coding module formed to allow or to provide an electrical connection between the sample strip and the bio measuring meter.

According to a further aspect of the invention, there is provided a bio measuring system for analysing an analyte, comprising at least one coding module with at least one code, preferably of the above described type and comprising a bio measuring meter, preferably of the above described type, with means for receiving the at least one code from the the coding module. The code ciphers at least one parameter value that is used in controlling the operation of the bio measuring meter, for example in control-ling the execution of an algorithm performed by the meter that enables determination of an analyte concentration value. The at least one code is represented by at least one figured element and the bio measuring meter comprises means for measuring at least one figured element representing the code.

The bio measuring system can comprise a set of coding modules, each having a different code being associated with a certain batch of sample strips.

According to a further aspect of the invention, there is provided a bio measuring test set, comprising at least one test strip, and comprising a coding module with at least one code, preferably of the above described type, being associated with the at least one test strip and pluggable into a bio measuring meter. The code ciphers at least one parameter value that is used in controlling the operation of the bio measuring meter when analysing the test strip, for example in controlling the execution of an algorithm performed by the meter that enables determination of an analyte concentration value. The at least one code is represented by at least one figured element.

Usually, a bio measuring test set comprising one coding module and a plurality of samples strips form a commercial unit which is sold together in one package.

According to a further aspect of the invention, there is provided a method for operating a bio measuring meter, preferably of the above described type, comprising the steps of (i) inserting a coding module with at least one code into the bio measuring meter; (ii) detecting the at least one code; (iii) determining at least one parameter value used for control-ling operation of the meter; (iv) inserting a sample strip and adding a biologic sample; and (v) analysing the sample on the basis of the at least one parameter value. The detecting of the at least one code is carried out by measuring at least one figured element arranged on the module.

Although the present invention is presented in the context of a clinical or diagnostic instrument, it has utility in calibration of other medical measurement devices as well.

The present invention may be more fully understood by referring to the following detailed description of illustrative embodiments thereof and the accompanying drawings thereof.

The above contents and advantages of the present invention will become more readily apparent to those ordinarily skilled in the art after reviewing the following detailed descriptions and accompanying drawings, in which:

BRIEF DESCRIPTION OF THE DRAWINGS

FIGS. 9a-9g are schematic views of different embodiments of figured elements on a sample strip according to the present invention.

DETAILED DESCRIPTION OF THE PREFERRED EMBODIMENT

Figure 1A:
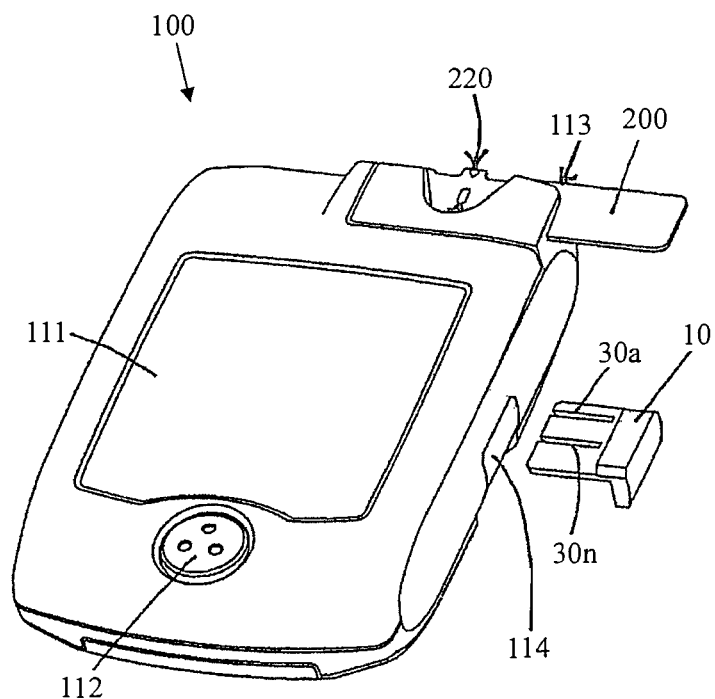
FIG. 1a is a perspective top view of a first example of a bio measuring meter incorporating the present invention.

Referring to FIG. 1, a bio measuring meter 100 has a display 111, an operation button 112 and a receptacle 113 able to receive a disposable sample strip 200. The sample strip 200 has a reaction zone which contains conductive electrodes. A reactant layer (not shown) is formed in the reaction zone to cover the electrodes. An analyte-containing fluid, for example a drop of blood, can be dripped on a substance entrance 220.

The bio measuring meter 100 further has a second receptacle 114 for receiving a coding module 10, which is inserted into the receptacle 114 of the bio measuring meter 100.

When the coding module 10 is plugged into the slot 114 of the bio measuring meter 100, measuring means of the bio measuring meter 100 get into contact with figured elements 30a, 30b, . . . 30n of the coding module 10.

Figure 1B:
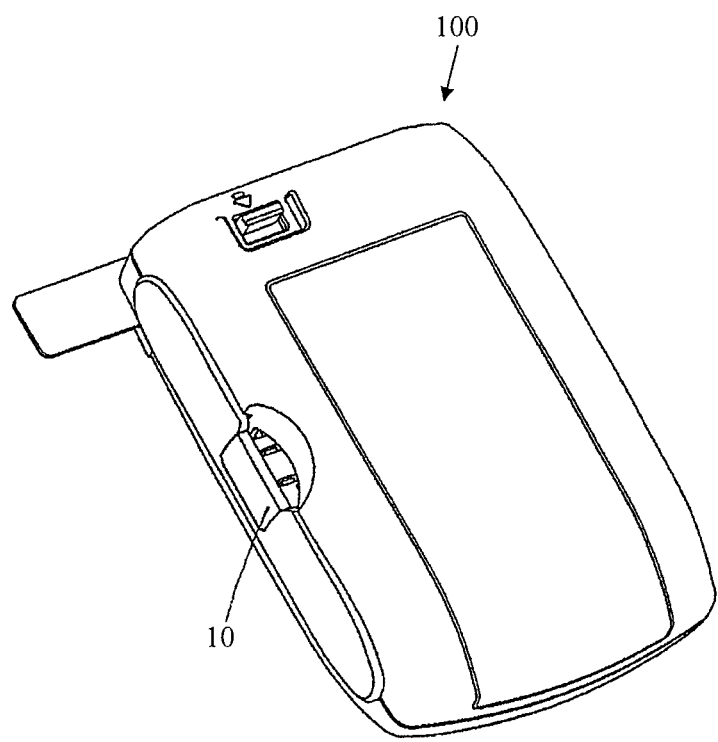
FIG. 1b is a perspective bottom view of a first example of a bio measuring meter incorporating the present invention.

FIG. 1b is a perspective bottom view of a first example of a bio measuring meter 100 with the inserted coding module 10.

Figure 2:
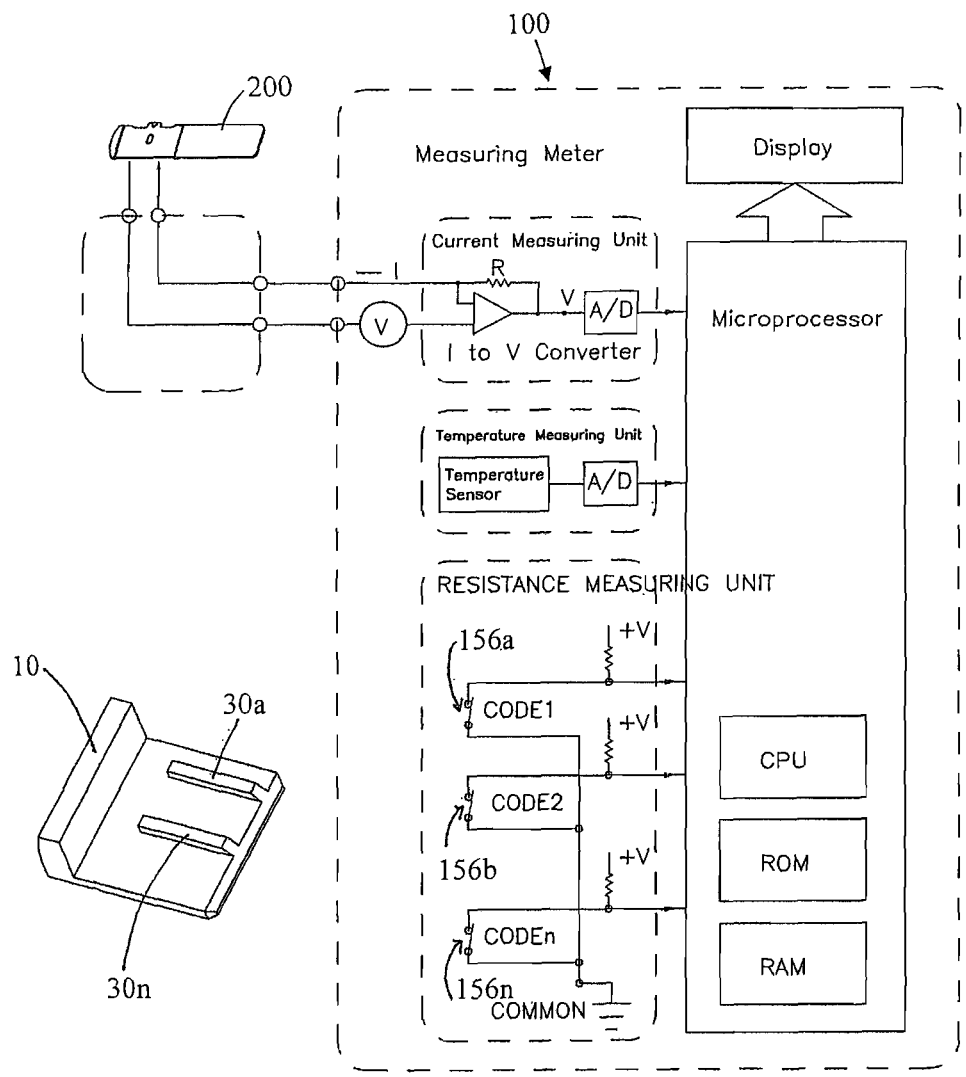
FIG. 2 is a schematic representation of a first embodiment of the present invention.

FIG. 2 schematically shows a meter 100 with a coding module 10 according to the present invention and with a test strip 200. The meter 100 comprises standard components such as a microprocessor with a central processing unit, a read-only memory and a random accessible memory, a display, a current measuring unit, an electrode working voltage supply unit and a temperature measuring unit. Those elements are standard in state of the art devices. In addition, the meter comprises a resistance measuring unit 150 which on the one hand is in operative connection with the microprocessor and on the other hand is connected to switches 156a, 156b, . . . , 156n for measuring figured elements 30a, 30b, . . . 30n in the coding module 10. The arrangement of figured elements 30a to 30n ciphers a certain code as will be shown hereinafter. Detection of the figured elements 30a, 30b, . . . 30n is made in a manner known to those skilled in the art, in particular by measuring a current in order to determine whether the switches 156a, 156b, . . . , 156n are open or closed. Analog/digital converters are used to transmit the current values to the micro-processor.

Figure 3A:
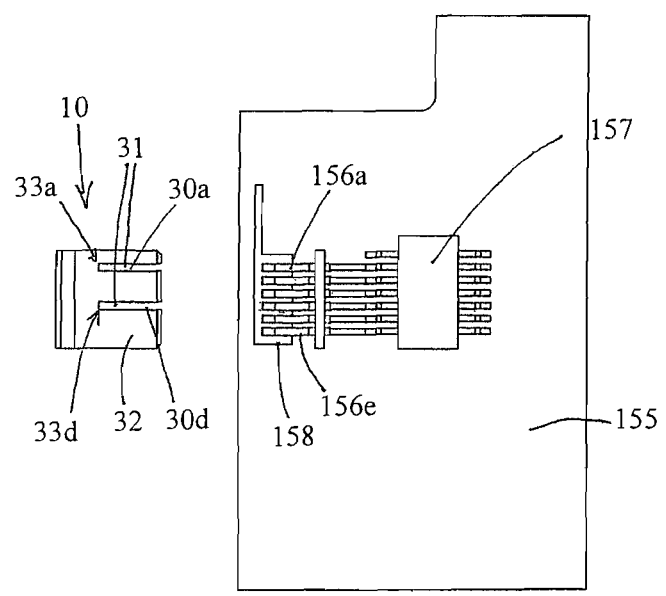
FIG. 3a is a top view of a first example of a coding module according to the present invention and corresponding switches of a meter according to the present invention.

FIG. 3a is a top view of a first example of a coding module 10 and measuring means 155 in form of five switches 156a, 156b, . . . , 156e of a meter. The switches 156a, 156b, . . . , 156e are in electrical contact with a common potential at a conductor 157. Without the coding module 10 being inserted, the switches 156a, 156b, . . . , 156e are in contact with a second conductor 158. Thus all switches 156a, 156b, . . . , 156e are "closed" able to allow passing a predefined current.

The coding module 10 in FIG. 3a has figured elements 30a, 30b, . . . , 30e in the form of cuts 31, which are arranged in a coding area 32 at certain positions 33a, . . . , 33e of the coding module 10. The number and the arrangement of the cuts represent a five-digit binary code.

Figure 3B:
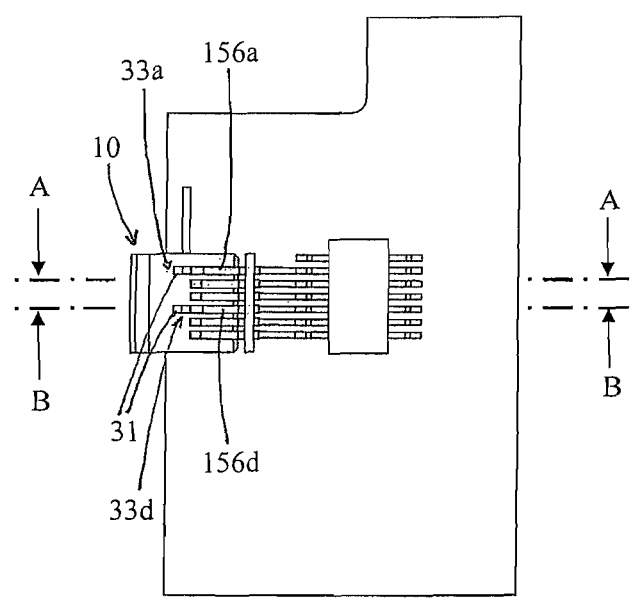
FIG. 3b is a top view of the example of FIG. 3a with a coding module inserted in the meter.

When the coding module 10 is inserted in the bio measuring meter 100, the figured elements 30a, 30b, . . . , 30e come into contact with the measuring means 155 as shown in FIG. 3b.

Each position 33a, . . . , 33e of a figured element 30a, 30b, . . . , 30n corresponds to a switch 156a, 156b, . . . , 156e. All switches 156a, 156b, . . . , 156e are opened, i.e. the contact between the conductors 158 and 157 is interrupted, by inserting the coding module 10 except those switches 156a and 156d, at which corresponding positions 33a, 33d cuts 31 are arranged on the coding module 10.

A current is thus flowing through switches 156a, 156d. This current can be sensed by measuring the voltage difference across a resistor, not explicitly shown in this Figure, connected in series with the switches.

Figure 4A:
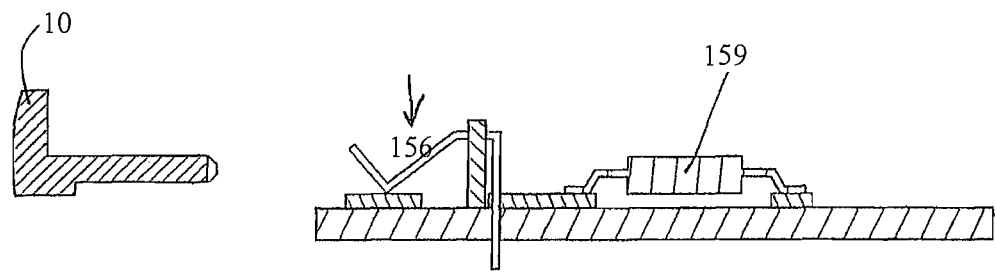
FIG. 4a is a side view of a switch and a coding module.

FIG. 4a is a side view of a switch 156 and a coding module 10, when the coding module is not inserted. The switch 156 is in a closed position, resulting in a current. The current leads to a difference of potential across a resistance 159 connected in series with the switch 156.

Figure 4B:
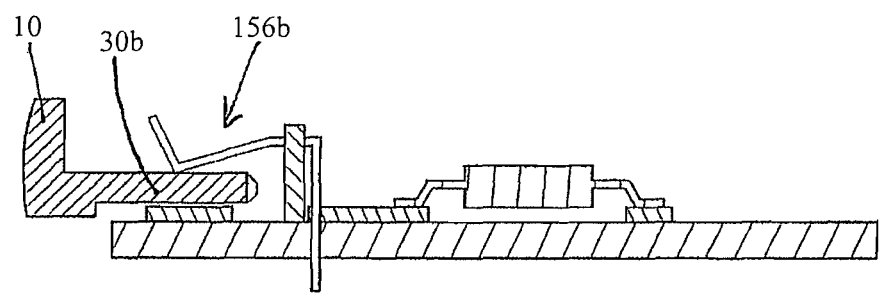
FIG. 4b is a sectional view of the switch engaged with a figured element from FIG. 3b along A-A.

FIG. 4b is a sectional view of FIG. 3 along A-A. Switch 156b is engaged with a figured element 30b of the coding module 10. The switch 156b now is in an open position, and the current is interrupted.

Figure 4C:
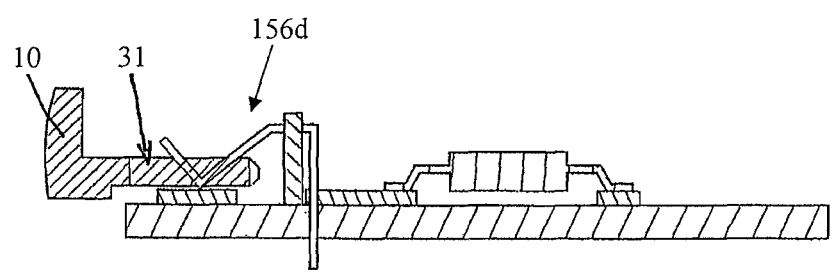
FIG. 4c is a sectional view of the switch engaged with a figured element from FIG. 3b along B-B.

FIG. 4c is a sectional view of FIG. 3 along B-B. Switch 156d of the coding module 10 meets a cut 31 at the position 33d associated with the switch 156d. Thus the switch 156d is in a closed position, when the coding module 10 is inserted.

The current flowing through switches 156a-156e of the meter 100 is related to the arrangement and the number of the cut 31. The code represented by the figured elements on the coding module 10 can thus be detected.

Figure 5A:
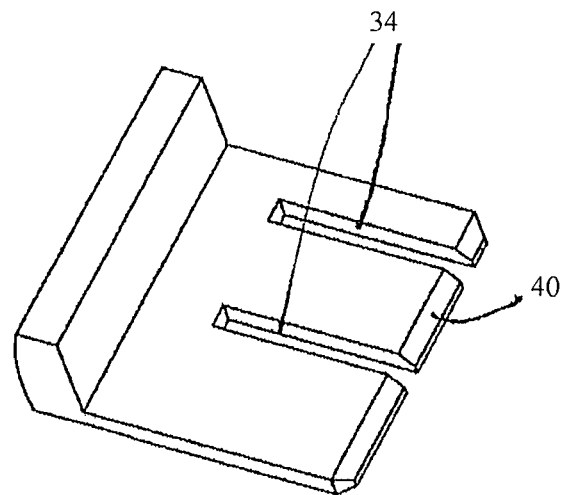
FIGS. 5a-5e are schematic views of different embodiments of figured elements on a coding module according to the present invention.
Figure 5B:
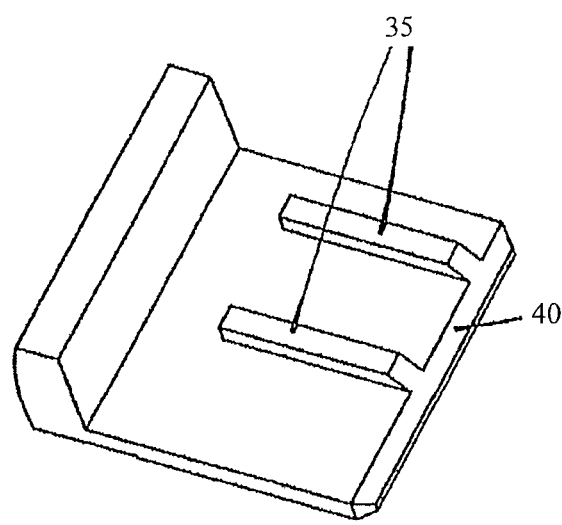
Figure 5C:
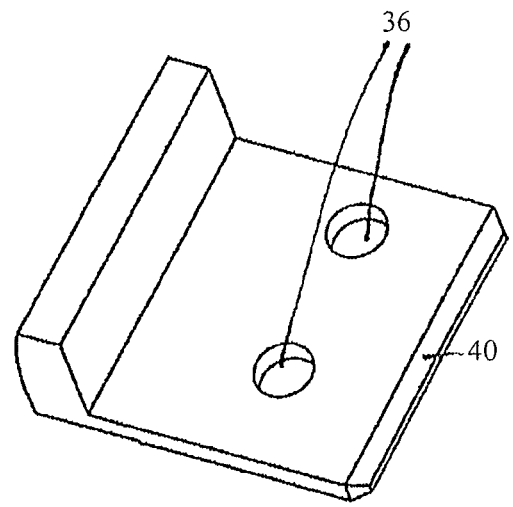
Figure 5D:
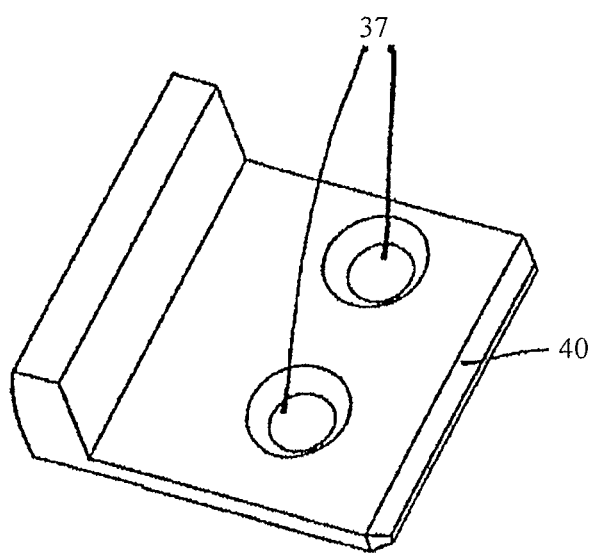
Figure 5E:
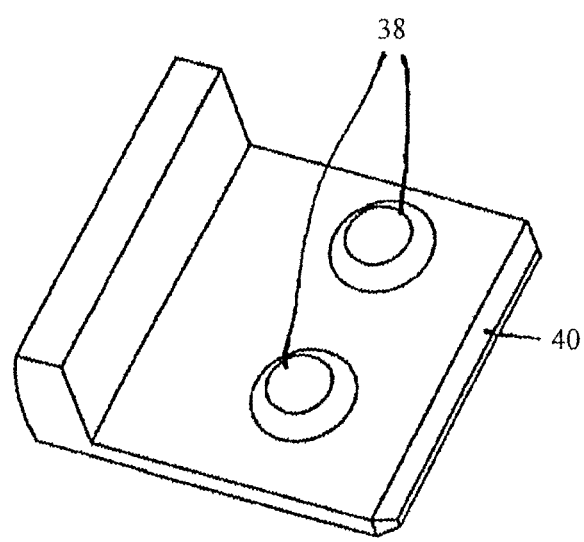

Different embodiments of figured elements on a coding module 10 are shown in FIGS. 5a to 5e, for example slots 34 in FIG. 5a, ribs 35 in FIG. 5b, holes 36 in FIG. 5c, dents 37 in FIG. 5d and bumps 38 in FIG. 5e.

The front area 40 of the coding module 10 is tapered to ease the insert and the opening of the switches.

Figure 6A:
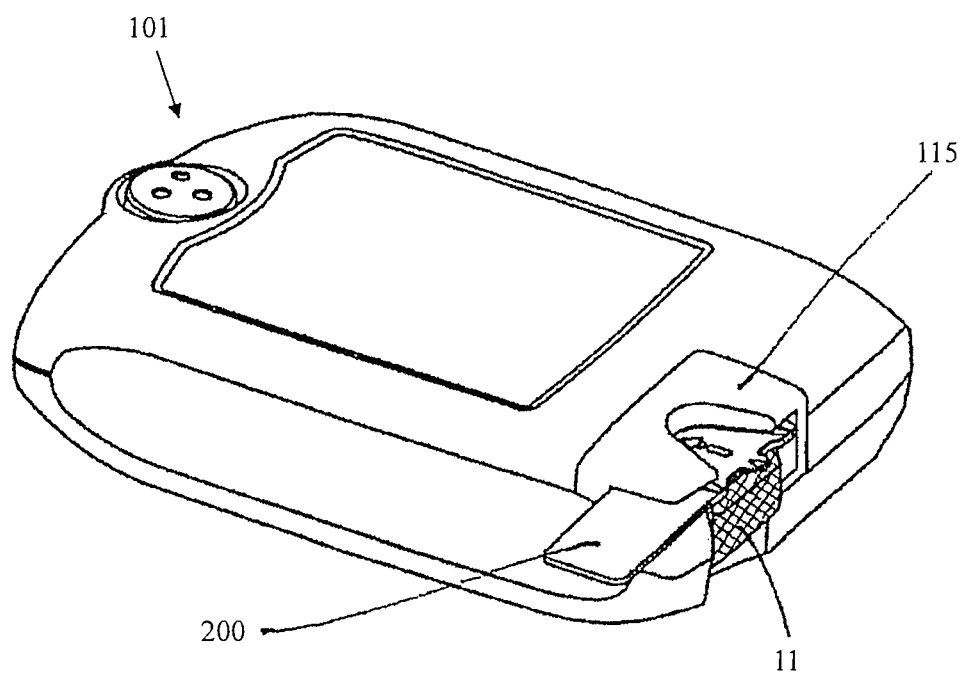
FIG. 6a is a perspective top view of a second example of a bio measuring meter incorporating the present invention with an inserted sample strip and coding module.
Figure 6B:
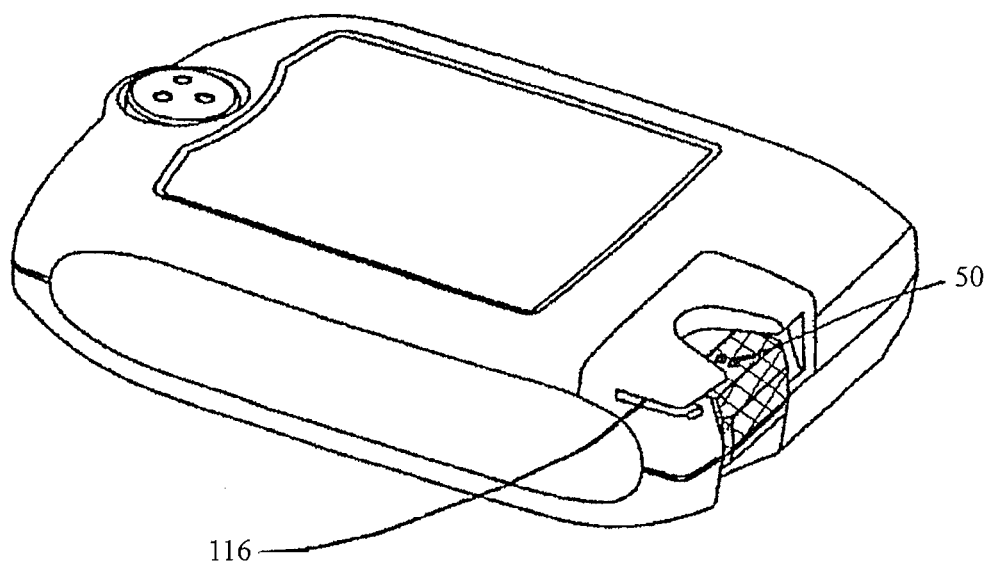
FIG. 6b is a perspective top view of the example of FIG. 6a without the sample strip.
Figure 6C:
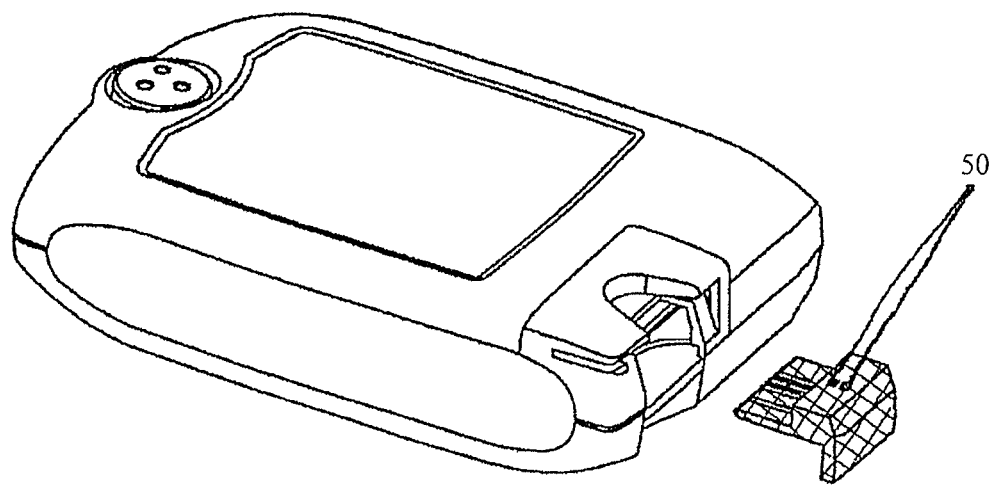
FIG. 6c is a perspective top view of the example of FIG. 6a with a removed module.

Referring to FIGS. 6a to 6c, in a second example of the present invention, the measuring meter 101 has one receptacle 115 for receiving the sample strip 200 and the coding module 11.

The coding module 11 allows an electrical connection between the bio measuring meter 101 and the sample strip 200. When the coding module 11 is plugged into the bio measuring meter 101, the sample strip can be inserted in a slot 116 of the same receptacle 115 and electrical contacts 50 on the coding module 11 get in contact with the electrodes of the sample strip 200.

Figure 7A:
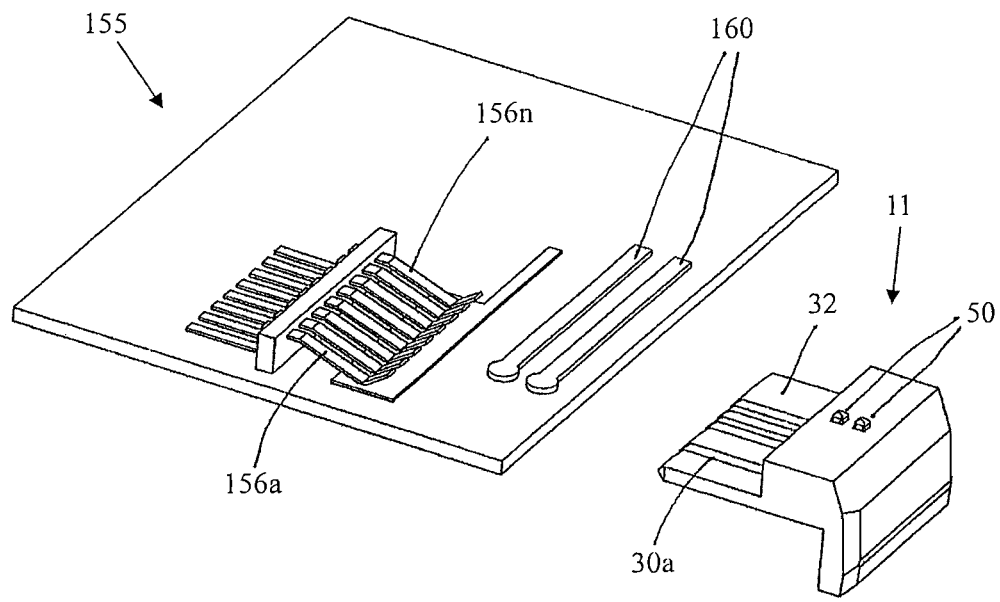
FIG. 7a is a perspective top view of a second example of a coding module according to the present invention and measuring means according to the present invention.

FIG. 7a is a perspective top view of the coding module 11 with a coding area 32 and electrical contacts 50 and measuring means 155. When the coding module 11 is inserted in the measuring meter, the coding area 32 with the figured elements 30a, 30b, . . . , 30n engages with the switches 156a, 156b, . . . , 156n, whereas the electrical contacts 50 get in contact with electrode contacts 160.

Figure 7B:
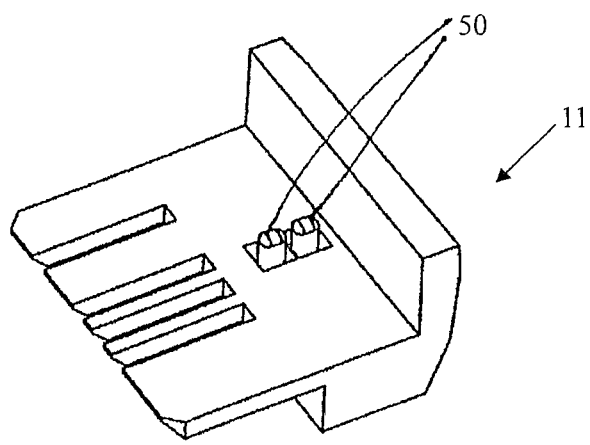
FIG. 7b is a perspective bottom view of a second example of a coding module according to the present invention.

FIG. 7b is a perspective bottom view of the coding module 11 with electrical contacts 50.

When the coding module 11 and the sample strip 200 are inserted in the measuring meter 101, the contacts 50 on the coding module 11 get in electrical contact with the electrodes of the sample strip. In a similar manner, contacts 160 of the meter 101 are brought into electrical contact with the contacts 50 of the coding module 11 and consequently with the electrodes of the sensor strip 200.

This embodiment makes sure that the meter can not be operated without a module 11 properly inserted.

Figure 8:
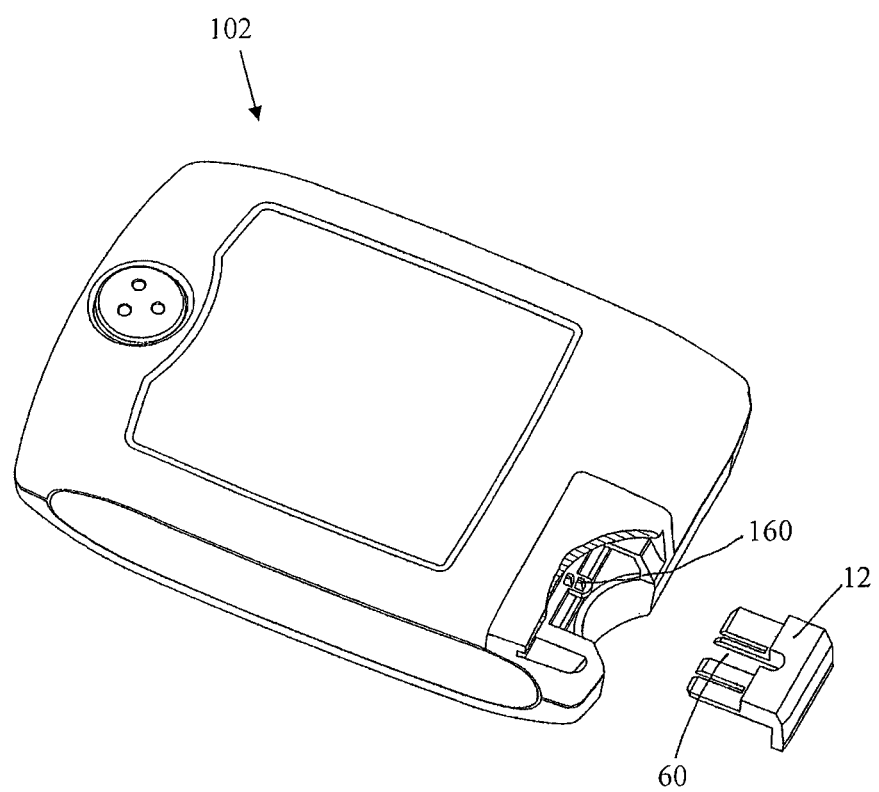
FIG. 8 is a perspective top view of a third example of a bio measuring meter incorporating the present invention.

Alternatively, the electrical contact between the electrodes on the sample strip and the electrode contacts 161 in the meter 102 can be made without conductive means on the coding modules 12, as shown in FIG. 8. The coding module 12 comprises a recess 60 which allows the electrode contacts 161 of the meter 102 to get in electrical connection with the electrodes of the sample strip, when the coding module 12 is inserted in the meter 102.

Different embodiments of figured elements integrally formed with the sample strip 200, i.e. the figured elements 91~97 are directly mounted on the sample strip 200, are shown in FIGS. 9a~9g. Each time while the sample strip 200 is inserted, the states of the switches are switched corresponding to the figured elements 91~97 and the code represented by the figured elements on the sample strip 200 can thus be detected.

While the invention has been described in terms of what is presently considered to be the most practical and preferred embodiment, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A bio measuring meter, comprising:
a receptacle and a plurality of switches configured to be switched upon insertion of a removable coding module including at least one figured element into the receptacle, the at least one figured element configured to switch one or more of the plurality of switches between a closed and open state, and through the at least one figured element the removable coding module defines a code employed in controlling the operation of the bio measuring meter, the receptacle configured to separately receive the removable coding module and a sample strip;
wherein the sample strip is of a type of sample strip the code employed in controlling the operation of the bio measuring meter corresponds to the type of sample strip, the sample strip includes an electrode, the removable coding module includes a first electrical contact electrically connected to a second electrical contact, and the bio measuring meter includes a bio measuring meter contact, and when both the sample strip and the removable coding module are inserted into the receptacle, the electrode contacts the first electrical contact and the second electrical contact contacts the bio measuring meter contact.

2. A bio measuring meter as claimed in claim 1 further comprising:
a memory storing plural parameters associated with the code; and
a microprocessor electrically connected to the memory and configured to obtain one or more parameter from the plural parameters according to the code.

3. A bio measuring meter as claimed in claim 1, wherein one or more of the at least one figured element is selected from a group consisting of a projecting element, a protrusion, a saw-toothed element, a rack, a pin, a notch, a cut, a recess, a through hole and a plane plate.

4. A bio measuring meter as claimed in claim 1, wherein the code is represented by a number and an arrangement of the figured elements.

5. An adjusting method for a bio measuring meter including a receptacle configured to separately receive a sample strip and a removable coding module, a memory, a processor, and an electrode contact, the method comprising:
inserting into the receptacle the sample strip, wherein the sample strip is of a type of sample strip and comprises an electrode;
inserting into the receptacle the removable coding module, wherein the removable coding module is separate from the sample strip, and comprises a first electrical contact electrically connected to a second electrical contact and at least one figured element, the at least one figured element defining a code employed in controlling the operation of the bio measuring meter, the code corresponding to the type of sample strip, and after inserting the sample strip and inserting the coding module, the electrode contacts the first electrical contact, and the second electrical contact contacts the electrode contact of the bio measuring meter;
obtaining an adjustment parameter from a look-up table stored in the memory based on the code; and
adjusting the bio measuring meter according to the parameter.

6. A method as claimed in claim 5 further comprising a step of:
obtaining a plurality of parameters corresponding to the code.

7. A method for operating the bio measuring meter as claimed in claim 5 further comprising:
placing a sample on the sample strip and analyzing the sample on the basis of the code.

8. A method as claimed in claim 5, wherein the at least one figured element includes a shape or surface texture defining the code.

9. A method as claimed in claim 5, wherein the code is represented by the number and arrangement of the at least one figure element and the bio measuring meter includes a plurality of switches configured to be switched upon insertion of the removable coding module, and upon inserting the removable coding module, the at least one figured element switches one or more of the plurality of switches between a closed and open state.

10. A bio measuring test set comprising:
at least one test strip comprising an electrode;
a bio measuring meter comprising a bio measuring meter contact; and
at least one removable coding module comprising a first electrical contact electrically connected to a second electrical contact; wherein
the bio measuring meter further comprises a receptacle configured to separately receive a test strip of the at least one test strip and a removable coding module of the at least one removable coding module, and a plurality of switches configured to be switched upon insertion the removable coding module,
the removable coding module including at least one figured element configured to switch one or more of the plurality of switches between a closed and open state, and through the at least one figured element, the removable coding module defines a code employed in controlling the operation of the bio measuring meter,
the sample strip is of a type of sample strip and the code employed in controlling the operation of the bio measuring meter corresponds to the type of sample strip, and
when both the sample strip and the removable coding module are inserted into the receptacle, the electrode contacts the first electrical contact, and the second electrical contact contacts the bio measuring meter contact.

\* \* \* \* \*